United States Patent [19]

Fujiu et al.

[11] Patent Number: 4,708,652

[45] Date of Patent: Nov. 24, 1987

[54] APATITE COMPOSITE CERAMICS

[75] Inventors: Takamitsu Fujiu, Tokyo; Masaaki Mochida; Makoto Ogino, both of Kawasaki, all of Japan

[73] Assignee: Nippon Kogaku K. K., Tokyo, Japan

[21] Appl. No.: 810,604

[22] Filed: Dec. 19, 1985

Related U.S. Application Data

[63] Continuation-in-part of Ser. No. 681,185, Dec. 13, 1984, abandoned.

[30] Foreign Application Priority Data

Mar. 6, 1984 [JP] Japan .................................. 59-42474

[51] Int. Cl.$^4$ .......................... A61C 8/00; C03C 10/16
[52] U.S. Cl. ..................................... 433/201.1; 501/1; 501/10; 501/17; 501/32; 501/57; 623/18; 106/35
[58] Field of Search ................. 106/35; 501/1, 10, 32, 501/63, 17, 57, 72; 3/1.9; 623/18; 433/201.1

[56] References Cited

U.S. PATENT DOCUMENTS 4,103,002  7/1978  Hench et al. ................ 428/155 OR
4,135,935  1/1979  Pfeil et al. ...................... 106/35 OR
4,437,192  2/1984  Fujiu et al. ....................... 3/1.9 OR

FOREIGN PATENT DOCUMENTS 4158099  5/1977  Japan .

Primary Examiner—Mark L. Bell
Assistant Examiner—Karl Group
Attorney, Agent, or Firm—Shapiro and Shapiro

[57] ABSTRACT

This invention provides a novel apatite composite ceramic useful for implants such as artificial dental root, artificial bone or the like. The apatite composite ceramic comprises an interconnected structure of fluorapatite phase and an at least partially crystallized biologically active glass phase, which ceramic is obtained by reaction-sintering at a sintering temperature of 700°–1100° C. at a pressure of at least atmospheric pressure a powder mixture of a synthetic hydroxyapatite (A) and a biologically active glass (B) containing fluoride ions and having a crystallization temperature below the sintering temperature in a weight ratio of A/B ranging from 60/40 to 30/70. The reaction-sintered material has excellent biological affinity and high mechanical strength.

6 Claims, 2 Drawing Figures

APATITE COMPOSITE CERAMICS

CROSS REFERENCE TO RELATED APPLICATION

This is a continuation-in-part of application Ser. No. 681,185, filed Dec. 13, 1984 now abandoned.

BACKGROUND OF THE INVENTION

1. Field of the Invention

The present invention relates to an apatite composite ceramic which is a useful material especially for artificial dental root, artificial bone and the like.

2. Description of the Prior Art

In recent years intensive studies have been made on implants such as artificial dental root and artificial bone. Substantial efforts have been made to search for those materials which enable provision of such implants with not only good biological affinity (referred to as affinity to live bone hereinafter) but also high mechanical strength and, consequently, a long effective life.

A representative known material for implantation is sintered-apatite. As the starting material of the sintered-apatite there is used a synthetic hydroxyapatite the composition of which is essentially the same as the main inorganic component of bone. The sintered-apatite obtained from the synthetic hydroxyapatite is, therefore, excellent in biological affinity.

On the other hand, when the sintered-apatite is to be used as implant material, the sintering must be carried out at a temperature as high as possible, for instance, at 1400° C. in order to obtain the necessary high mechanical strength. However, it has been known to those skilled in the art that the biological affinity is reduced when the sintering is carried out at such high temperature. This is because, during the sintering, there occurs a change of chemical structure from hydroxyapatite to oxyapatite with elimination of the hydroxy group. In this connection it has been reported that in order to obtain high biological affinity it is desirable to carry out the sintering at a temperature lower than 1100° C., in particular, in the range of 700° to 900° C.

Many attempts have already been made to find means for improving the mechanical strength of sintered-apatite while avoiding the use of such high sintering temperature adverse to the biological affinity. As a solution to the problem it has been proposed to add to the synthetic hydroxyapatite powder some particular additives such as CaO, MgO, $Al_2O_3$ and other reinforcing materials aiming at improvement of mechanical strength and also achievement of lower sintering temperature (cf. Japanese Patent Application Publication No. 40,776/1982).

Obviously, the solution as mentioned above is not satisfactory and cannot solve the problem completely. The additives and reinforcing agents themselves have no biological affinity. If such materials are added to the synthetic hydroxyapatite powder, the sintered-apatite obtained from the mixture will exhibit biological affinity degraded by the additives.

Because of the difficulties mentioned above, there has not yet been provided any sintered-apatite which satisfies the requirements of good biological affinity and high mechanical strength at the same time.

SUMMARY OF THE INVENTION

Accordingly an object of the present invention is to provide a sintered-apatite ceramic material which is excellent in not only biological affinity but also mechanical strength and, therefore, which can be used advantageously as implant material.

In order to attain this object, the inventors of the present invention have conducted extensive research and experimentation and have discovered that the desired material of good biological affinity and high mechanical strength can be obtained by reaction sintering at a sintering temperature of 700°–1100° C. at a pressure of at least atmospheric pressure a powder mixture of a synthetic hydroxyapatite (A) and a biologically active glass (B) containing fluoride ions and having a crystallization temperature below the sintering temperature in a weight ratio of A/B ranging from 60/40 to 30/70.

In the powder mixture, the biologically active glass serves as binder and, therefore, the product obtained by sintering the mixture has sufficiently high mechanical strength even when the sintering is carried out at a lower temperature than that required according to the prior art. Since a relatively low sintering temperature is used, the above-mentioned undesirable conversion of hydroxyapatite to oxyapatite during sintering is obviated and, consequently, there is no reduction of biological affinity of the apatite.

The resulting reaction-sintered product has an interconnected structure of a fluorapatite phase and a biologically active glass phase. The fluorapatite must have been produced by a reaction of the fluoride ions with the hydroxyapatite during the sintering. Thus, the sintering will be referred to as "reaction-sintering" hereinafter.

The biologically active glass containing fluoride ions serves as a reactant for changing the hydroxyapatite into the fluorapatite. It is believed that the fluoride ions react with the hydroxyapatite prior to the other components. The oxyapatite is seldom produced during the reaction-sintering.

Advantageously, the fluorapatite of the reaction product has high mechanical strength as compared with the hydroxyapatite. When the hydroxyapatite is used as a starting material and changed into the fluorapatite by the reaction-sintering, the mechanical strength of the resultant product is higher than that of the product obtained with fluorapatite as a starting material. In this regard, reference should be made to the Tables 1 and 3 as described later.

It should be understood that the existence of fluoride ions in the biologically active glass is important. When hydroxyapatite and the biologically active glass not containing fluoride ions were used as starting materials and subjected to the sintering process, complete decomposition of the hydroxyapatite was observed at a temperature of 400° to 500° C. in its X-ray diffraction spectrum. Such a sintered product has weak biological affinity and low mechanical strength. The fluoride ions in the biologically active glass may change the hydroxyapatite into the stable fluorapatite at a relatively low temperature so as to prevent the apatite phase from decomposing.

Furthermore, since the biologically active glass of the present invention has a crystallization temperature below the sintering temperature, the glass will be at least partially crystallized during the reaction-sintering. The crystallized glass phase in the sintered product contributes the high mechanical strength of the sintered product, which is not the case with non-crystalline glass.

Further, since the material used as binder is not common glass but biologically active glass, there is no problem of reduction of biological affinity of the sintered product on the whole, as is caused by adding the above-mentioned additives and/or reinforcing agents according to the prior art.

Accordingly, the subject of the present invention based on the above finding is an apatite composite ceramic comprising an interconnected structure of fluorapatite phase and an at least partially crystallized biologically active glass phase, which ceramic is obtained by reaction-sintering at a sintering temperature of 700°–1100° C. at a pressure of at least atmospheric pressure a powder mixture of a synthetic hydroxyapatite (A) and a biologically active glass (B) containing fluoride ions and having a crystallization temperature below the sintering temperature in a weight ratio of A/B ranging from 60/40 to 30/70.

The synthetic hydroxyapatite used as the powder (A) in the invention is a material whose composition is the same or similar to the natural hydroxyapatite $Ca_{10}(PO_4)_6(OH)_2$. It is known per se and can be prepared according to a method known per se. For example, the synthetic hydroxyapatite powder can be prepared in the following manner:

Calcium ion and phosphate ion are reacted in an aqueous solution to produce a precipitate of calcium phosphate having a Ca/P atom number ratio in the range of 1.5 to 1.67. The precipitate is filtered, dried and milled. The pulverized product is then calcinated at 800° C. to fine hydroxyapatite powder. The hydroxyapatite powder suitably used as the component (A) in the invention has a particle size in the range of from 200 to 500 mesh.

The biologically active glass containing fluoride ions used as the component (B) in the invention is also known per se. It is a kind of glass having biological affinity and able to chemically combine with bone. An example of such biologically active glass (B) is selected from the scope of the following composition (cf. U.S. Pat. No. 4,437,192):

| $SiO_2$ | 35–60 mol % |
| --- | --- |
| $B_2O_3$ | 0–15 mol % |
| $Na_2O$ | 10–30 mol % |
| CaO | 5–40 mol % |
| $TiO_2$ | 0–10 mol % |
| $P_2O_5$ | 0–15 mol % |
| $K_2O$ | 0–20 mol % |
| $Li_2O$ | 0–10 mol % |
| MgO | 0–5 mol % |
| $Al_2O_3 + ZrO_2 + Nb_2O_5$ | 0–8 mol % |
| $La_2O_3 + Ta_2O_5 + Y_2O_3$ | 0–8 mol % |
| $F_2$ | 5–20 mol %. |

The biologically active glass must have a crystallization temperature below the sintering temperature of 700° to 1100° C. Determination of the crystallization temperature of glass may be readily conducted by a differential thermal analysis.

The biologically active glass is milled into powder (B) in a conventional manner. The preferred range of particle size of the powder (B) is from 200 to 500 mesh.

The powder (A) and the powder (B) are then mixed together in a conventional manner at a weight ratio of A/B=60/40 to 30/70. This range of A/B mixing ratio has been determined experimentally and constitutes an important feature of the present invention. The results of our experiments have shown that when the powder (A) and the powder (B) are mixed together in a ratio outside of the above range, there is obtained a reaction-sintered product whose mechanical strength is not so good as compared with the product from the powder (A) alone or the powder (B) alone.

The sintering of the mixture of the powders (A) and (B) is carried out employing a conventional method. For example, the mixture is at first cold-pressed in a metal mold using a pressure of 1 to 2 t/cm$^2$ and then sintered generally at a temperature of 700° to 1100° C., preferably 700° to 900° C. for 2 to 5 hours at atomospheric pressure. A sintering temperature over 1100° C. is unsuitable. Otherwise a substantial amount of the hydroxyapatite will be converted into oxyapatite.

The reaction-sintered product obtained in the above manner, that is, the apatite composite ceramics according to the invention may have an improved mechanical strength by 30 to 40% on average if further sintered by hot-pressing. The hot-press sintering is generally carried out by holding the product for ten minutes to three hours at a temperature of 700° to 1100° C., preferably 750° to 950° C. under a pressure of 50 to 200 kg/cm$^2$. In another method, the cold-pressed mixture without the sintering at atmospheric pressure may be sintered directly by hot-pressing so as to change into a sintered product also having an improved mechanical strength. A refractory mold such as a graphite mold is suitably used for the hot-press sintering. Preferably, the mold is pre-coated with mold lubricant such as BN powder for prevention against sticking of the product.

The improvement in the mechanical strength of the sintered product by such hot pressing is apparently brought about because the softened powder (B) eliminates fine pores or microcracks in the product by viscous flow. This process does not affect the biological affinity of the product.

The reaction-sintered product obtained in the above manner, that is, the apatite composite ceramic according to the invention may be used directly as an implant if the product matches with the intended implant in shape and size. If it does not match, the sintered body is processed into an implant by cutting and polishing.

The application of the apatite composite ceramic of the present invention is not limited to implants only. It may be used also as a raw material for screws and nuts to be used for provisionally fastening an implant, especially a subperiostial implant to an alveolar bone. In a completely different application, the product according to the invention is useful also as a catalyst for chemical reaction. Furthermore, it may be used as a raw material for the preparation of substrate members.

The apatite composite ceramic according to the invention is characterized by its high mechanical strength and good biological affinity. An implant made of the apatite composite ceramic has many advantages over the sintered-apatite according to the prior art.

Using the ceramic according to the invention, one can reduce the diameter of the implant as compared with the implant of the prior art for the same strength. Furthermore, one can obtain an implant having an improved implant-bone bonding strength. Since a high implant-bone bonding strength is assured without the aid of any mechanical bonding force, it is no longer necessary to form the implant into a complicated shape as conventionally required to obtain the mechanical bonding force. In addition, owing to the high biological affinity, the implant according to the invention exhibits a high implant-bone bonding strength even when the contact area between the implant and the bone is smaller. Therefore, the implant need not have a large contact area. The implant may be so formed as to have a small contact area and a slender and uniform shape (which is very easy to make). By virtue of these advantages, dental implants made from the apatite composite ceramics according to the invention are applicable to various cases for which an implant of the prior art could not be used. The dental implant according to the invention offers yet another advantage in that it simplifies the operation for implantation.

A further advantage of the sintered material according to the invention is found in that the coefficient of thermal expansion of the sintered body can be controlled as a whole by suitably changing the composition of the glass powder (B) added to the component (A). It is, therefore, possible to prepare an apatite composite ceramic containing a metal core in which the ceramic and the metal core have the same coefficient of thermal expansion and are joined together simultaneously with the sintering. Obviously such sintered material containing a metal core has a mechanical strength far higher than a similar sintered material without a metal core.

BRIEF DESCRIPTION OF THE DRAWINGS

FIG. 1 shows an interconnected structure of a sample sintered at atomspheric pressure;

FIG. 2 shows an interconnected structure of a hot pressing sample.

DESCRIPTION OF PREFERRED EMBODIMENT

Figure 1:
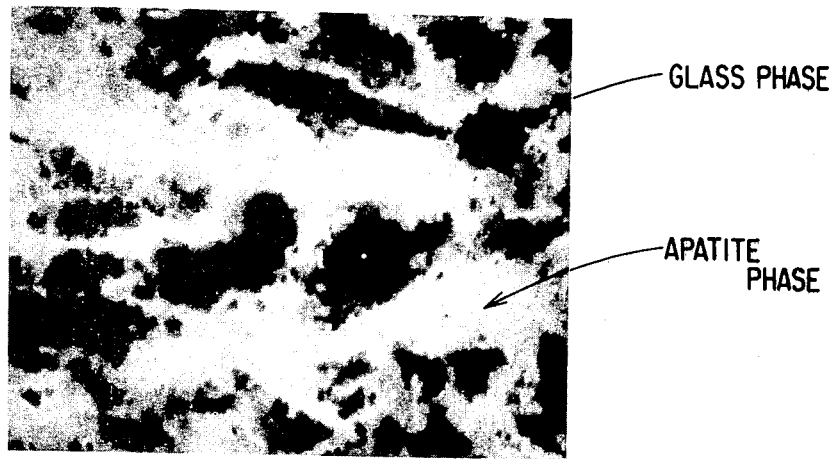
FIGS. 1 and 2 are photomicrographs of sintered products in accordance with the invention.

Examples (1) Preparation of synthetic hydroxyapatite powder (A)

10l aqueous solution containing 0.3 mol/l of phosphoric acid was added to 10 l aqueous suspension containing 0.5 mol/l of $Ca(OH)_2$. The mixture was stirred to react at 20° C. for an hour. After completing the reaction stirring was stopped and the mixture was allowed to stand at the same temperature for 48 hrs. for aging. After aging, the reaction product was washed with water, filtered, dried and ground into fine particles.

A sample of the particles was examined by powder X-ray diffraction method and chemical analysis. It was found that the product was microcrystalline calcium phosphate having a Ca/P ratio of about 1.6 and a structure similar to hydroxyapatite.

The calcium phosphate was milled into fine powder and the powder was passed through a 200 mesh screen to separate from larger particles than 200 mesh.

(2) Preparation of biologically active glass powder containing fluoride ions (B)

A powder mixture containing 46.1 mol% of $SiO_2$, 24.4 mol% of $Na_2O$, 13.5 mol% of $CaO$, 13.4 mol% of $CaF_2$ and 2.6 mol% of $P_2O_5$ was heated to melt in a platinum pot. After clarification the molten mass was annealed to form a biologically active glass (melting point: ca. 1050° C.; crystallization temperature: ca. 685° C.; $F_2$ content: 11.8 mol%).

The glass thus obtained was milled into powder in a conventional manner and the glass powder was passed through a 500 mesh screen to separate from larger particles than 500 mesh.

(3) Preparation of apatite composite ceramic (reaction-sintered product)

The powders (A) and (B) prepared in the above steps (1) and (2) were mixed together in the mixing ratios shown in Table 1 appearing hereinafter. 200 g of the mixture was weighed out and 200 cc of ethanol was added to it. In a pot mill the mixture and the ethanol were well mixed for two hours. The resulting mixture was filtered and dried by a drier at 110° C. to evaporate off the remaining ethanol.

The powder thus obtained was charged into a metal press-mold and cold-pressed under a pressure of 1.5 $t/cm^2$.

The pressure-molded mixture was then brought up to 900° C. at a heating rate of 200° C./hour and sintered for two hours at 900° C. Thereafter it was cooled down at a cooling rate of 500° C./hour.

In this manner, many samples of sintered products having different ratios of A/B were prepared as shown in Table 1.

Photomicrographs of fractures of the sintered product sample Nos. 4 to 7 confirmed that the reaction-sintered products had the interconnected structure, and that the glass phase was almost or at least partially crystallized.

Furthermore, the sintered products were analyzed by means of electron microprobe analysis, inforced spectrochemical analysis and scanning electron microscope. These analyses clearly showed that almost all of the hydroxyapatite had changed into fluorapatite.

Measurement of Mechanical Strength

The samples were tested for four-point bending strength according to the standard test method of JIS: R 1601. The results of the measurements are shown in Table 1.

Measurement of Affinity to Bone

Each sample obtained in the above manner was cut and shaped into a truncated-conical implant of 2 mm in base diameter, 5 mm in height and 1/20 in taper. The implant was implanted in a thighbone of a rabbit. Eight weeks after the implantation, the rabbit was dispatched and the implant-thighbone bonding strength was measured by the push-out test with a compression tester. The results of the measurements are shown in Table 1 as a measure of the biological affinity of the implant.

TABLE 1

| Sample No. | Comparative | | | Present Invention | | | | Comparative | |
|---|---|---|---|---|---|---|---|---|---|
| | 1 | 2 | 3 | 4 | 5 | 6 | 7 | 8 | 9 |
| Composition: | | | | | | | | | |
| weight ratio of powder A/B | 100/0 | 80/20 | 70/30 | 60/40 | 50/50 | 40/60 | 30/70 | 20/80 | 0/100 |
| Bending strength [kg/mm$^2$] | 2.0 | 0.8 | 1.2 | 10.0 | 17.2 | 14.1 | 9.2 | 7.8 | 7.0 |
| Biological | * | — | 3.1 | 3.1 | 3.5 | 3.9 | 3.1 | — | 3.1 |

TABLE 1-continued

| Sample No. | Comparative | | | Present Invention | | | | Comparative | |
|---|---|---|---|---|---|---|---|---|---|
| | 1 | 2 | 3 | 4 | 5 | 6 | 7 | 8 | 9 |
| affinity (bonding strength) [kg/mm$^2$] | | | | | | | | | |

(*The implant was broken by the push-out test and the measurement was impossible.)

As further comparative examples, the powder (A) alone was sintered at 1200° C. and at 1400° C. The samples obtained were tested for bending strength and bonding strength in the same manner as above. The measured values of bending strength were relatively high, 13 Kg/mm$^2$ for the sample sintered at 1200° C. and 15 Kg/mm$^2$ for the sample sintered at 1400° C. However, the values of bonding strength measured by the push-out test were low, 2.3 Kg/mm$^2$ for the former and 1.6 Kg/mm$^2$ for the latter. These low values of bonding strength mean that both of the samples are poor in biological affinity.

(4) Preparation of apatite composite ceramics by hot-pressing

The samples No. 4 to No. 7 as described in Table 1 were set in a mold of graphite with BN powder. Thereafter, the mold was heated up to 900° C. at a heating rate of 200° C./hour in nitrogen gas. The samples were pressed and held under a pressure of 120 Kg/cm$^2$ through a punch for two hours at 900° C. in the mold. Then, the samples in the mold were brought down to an atomspheric environment at a pressure drop rate of 60 Kg/cm$^2$·hour and at a cooling rate of 500° C./hour.

The hot-pressed samples obtained in the above manner were tested for their mechanical strength and affinity to bone. The results of the measurements are shown in Table 2.

TABLE 2

| Sample No. | Hot-pressed samples | | | |
|---|---|---|---|---|
| | 4 | 5 | 6 | 7 |
| Bending strength [kg/mm$^2$] | 16.3 | 25.1 | 19.8 | 14.6 |
| Biological affinity (bonding strength) [kg/mm$^2$] | 3.2 | 3.5 | 3.8 | 3.1 |

(Comparative Example Nos. 10-13)

(1) Preparation of fluorapatite 10 l aqueous solution containing 0.3 mol/l of phosphoric acid and 10 l aqueous solution containing 0.1 mol/l fluoric acid were added to 10 l aqueous suspension containing 0.5 mol/l of Ca(OH)$_2$. The mixture was stirred to react at 20° C. for an hour. After completing the reaction, stirring was stopped and the mixture was held in standing at the same temperature for 48 hours for aging. After aging, the reaction product was washed with water and filtered. According to powder X-ray diffraction method and chemical analysis, the product was microcrystalline calcium phosphate having a Ca/P ratio of about 1.6 and a structure similar to fluorapatite.

The calcium phosphate was milled into fine powder and the powder was passed through a 200 mesh screen to separate from larger particles than 200 mesh.

(2) Preparation of biologically active glass not containing fluoride ions

A powder mixture containing 46.1 mol% of SiO$_2$, 24.4 mol% of Na$_2$O, 26.9 mol% of CaO and 2.6 mol% of P$_2$O$_5$ was heated to melt in a platinum pot. After clarification, the molten mass was annealed to form a biologically active glass (melting point: ca. 1150° C.; crystallization temperature: ca. 685; F$_2$ content: O mol%).

The glass thus obtained was milled into powder in a conventional manner and the glass powder was passed through a 500 mesh screen to separate from larger particles than 500 mesh.

(3) Preparation of sintered product

The fluorapatite powder and the glass powder not containing fluoride ions were mixed together in the mixing ratio as shown in the following Table 3. The mixture was sintered in the same manner as in the examples of the present invention.

The sintered product was subjected to the measurement of the mechanical strength in accordance with the standard test method of JIS: R 1601 as described before. The results of the measurements are shown in Table 3.

TABLE 3

| Composition: | Comparative Sample No. | | | |
|---|---|---|---|---|
| | 10 | 11 | 12 | 13 |
| weight ratio of powder A/B | 60/40 | 50/50 | 40/60 | 30/70 |
| Bending strength kg/mm$^2$ | 9.0 | 15.5 | 12.5 | 8.3 |

Figure 2:
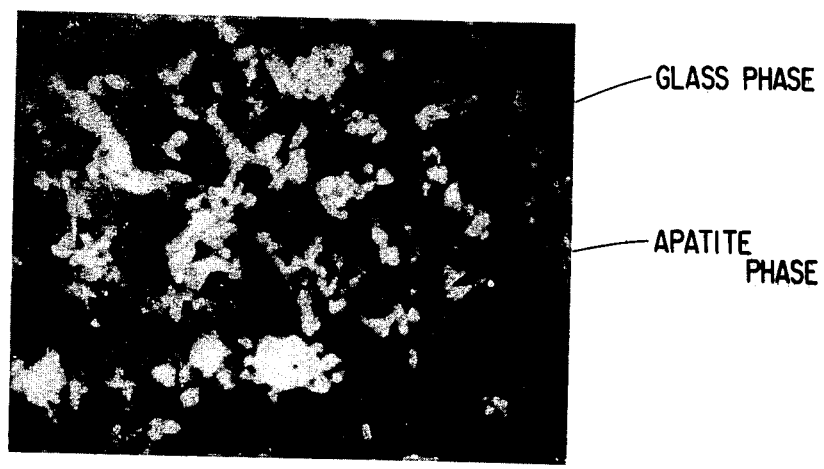

According to photomicrographs of the reaction-sintered products of the invention, the glass phase and the apatite phase are mixed with each other and interconnected within the same phase, respectively, as shown in FIGS. 1 and 2. That is, a darkened portion of the glass phase is continuously connected to one or more neighboring darkened portions of the glass phase, and the same is the case in the apatite phase as shown by white. Accordingly, the term "interconnected structure" is used with the above-defined meaning in the present specification and the claims.

The claims are:

1. An apatite composite ceramic comprising a fluorapatite phase and an at least partially crystallized biologically active glass phase, which ceramic is obtained by reaction-sintering at a sintering temperature of 900°–1100° C. at a pressure of at least atmospheric pressure a powder mixture of a synthetic hydroxyapatite (A) and a biologically active glass (B) which contains fluoride ions corresponding to F$_2$ of 5–20 mol% based on the glass (B) and which has a crystallization temperature below said sintering temperature, in a weight ratio of A/B ranging from 60/40 to 30/70.

2. An implant formed of the apatite composite ceramics as set forth in claim 1.

3. An implant according to claim 2, wherein said implant is a dental implant.

4. An apatite composite ceramic comprising a fluorapatite phase and an at least partially crystallized biologically active glass phase, which ceramic is obtained by reaction-sintering at a sintering temperature of 900°–1100° C. at a pressure of at least atmospheric pressure a powder mixture of a synthetic hydroxyapatite (A) and a biologically active glass (B) selected from the scope of the following composition:

| | |
|---|---|
| $SiO_2$ | 35–60 mol % |
| $B_2O_3$ | 0–15 mol % |
| $Na_2O$ | 10–30 mol % |
| CaO | 5–40 mol % |
| $TiO_2$ | 0–10 mol % |
| $P_2O_5$ | 0–15 mol % |
| $K_2O$ | 0–20 mol % |
| $Li_2O$ | 0–10 mol % |
| MgO | 0–5 mol % |
| $Al_2O_3 + ZrO_2 + Nb_2O_5$ | 0–8 mol % |
| $La_2O_3 + Ta_2O_5 + Y_2O_3$ | 0–8 mol % |
| $F_2$ | 5–20 mol % | said biologically active glass having a crystallization temperature below said sintering temperature, the weight ratio of A/B ranging from 60/40 to 30/70.

5. A process for preparing an apatite composite ceramic having a fluorapatite phase and an at least partially crystallized biologically active glass phase, comprising:

reaction-sintering at a sintering temperature of 900°–1100° C. and at a pressure of at least atmospheric pressure a powder mixture of a synthetic hydroxyapatite (A) and a biologically active glass (B) which contains fluoride ions corresponding to $F_2$ of 5–20 mol% based on the glass (B) and which has a crystallization temperature below said sintering temperature, in a weight ratio of A/B ranging from 60/40 to 30/70.

6. A process as set forth in claim 5, including hot-press sintering of said mixture.

* * * * *